United States Patent [19]

Eoga

[11] Patent Number: 4,499,001

[45] Date of Patent: Feb. 12, 1985

[54] CONTROLLED FADE EFFERVESCING CLEANSER

[75] Inventor: Anthony B. J. Eoga, Boonton, N.J.

[73] Assignee: Warner-Lambert Company, Morris Plains, N.J.

[21] Appl. No.: 585,654

[22] Filed: Mar. 2, 1984

Related U.S. Application Data

[63] Continuation of Ser. No. 251,030, Apr. 3, 1981, abandoned.

[51] Int. Cl.$^3$ .......................... C11D 3/40; C11D 7/10; C11D 7/12; C11D 7/18
[52] U.S. Cl. ........................................ 252/99; 252/95; 252/102; 252/103; 252/174; 252/186.43; 252/350
[58] Field of Search .............. 252/95, 99, 103, 186.43, 252/350, 174, 102

[56] References Cited

U.S. PATENT DOCUMENTS

| | | | |
|---|---|---|---|
| 3,243,377 | 3/1966 | Stolar | 252/95 |
| 3,337,466 | 8/1967 | Puetzer | 252/99 |
| 3,355,392 | 11/1967 | Cantor | 252/99 |
| 3,558,497 | 1/1971 | Lawes | 252/99 |
| 3,595,798 | 7/1971 | Leeds | 252/95 |
| 3,704,227 | 11/1972 | Hill | 252/99 X |

Primary Examiner—Dennis L. Albrecht
Attorney, Agent, or Firm—Daniel A. Scola, Jr.; Gary M. Nath

[57] ABSTRACT

A cleansing composition is disclosed with household and personal care applications and comprises a monopersulfate oxidizing agent and a halide bleaching promoter, to which is added an effervescence promoting compound comprising a perborate salt. The resulting composition is operable and capable of effervescing at an alkaline pH, at which it is also a more effective cleanser.

In a further embodiment, the above cleansing composition may include a colorant and a fade control agent comprising a compound providing a soluble halide ion for applications where it is desirable that the color provided by the colorant will fade within a given period of time. Small quantities of the fade control compound are effective, and do not disturb the desired initial color intensity of the solution provided by the colorant.

16 Claims, No Drawings

CONTROLLED FADE EFFERVESCING CLEANSER

This is a continuation of application Ser. No. 251,030, filed Apr. 3, 1981 now abandoned.

BACKGROUND OF THE INVENTION

1. Field of the Invention

The present invention relates generally to cleansers, and more particularly to those cleansers that include oxidizing and bleaching agents.

2. Description of the Prior Art

Cleanser compositions have for some time used oxidizing agents and bleaching agents in concert to remove visible stains from hard surfaces, while at the same time effecting the removal of scale or plaque build-up on those surfaces. Thus, cleaning compositions, prepared with abrasive materials for use as scouring cleansers, or alone for purpose of mild surface cleaning applications, have employed a variety of sulfate salts, eg. bisulfates, monopersulfates, and sulfates as detergents, oxidizers and the like, and have utilized alkali metal and alkaline earth metal halides as bleaches.

U.S. Pat No. 3,458,446 to Diaz discloses an abrasive cleansing composition that utilizes certain monopersulfate oxidizing agents in combination with a water-soluble bromide salt, in place of chlorine-liberating constituents conventionally employed in such compositions. The replacement of the chloride constituents by the bromide constituents was found to eliminate the unpleasant odor of chlorine. The composition disclosed in Diaz was primarily intended for use in powdered form, and utilized a variety of additives, such as detergents, builders and the like in its formulation.

The preparation of cleansers to be utilized in a solution for dipping, or soaking the articles to be cleaned therein, presents different problems from those that attend the preparation and use of cleansing compositions that are applied to the surface of the articles to be cleaned. Thus, whereas one may apply a composition, either in liquid or granular form, to a surface and may then agitate the surface to assist the cleaning operation, the employment of compositions that operate in a "passive" manner to serve as dipping solutions and the like, gives no indication of their efficacy, and of the period of their activity. In particular, cleansers utilized for the preparation of dipping solutions for dentures and the like, have conventionally exhibited an effervescent action in solution that assists in stain and plaque removal by providing a desired amount of agitation in the solution to promote cleansing activity. Also, such compositions have conventionally included colorants such as dyes, incorporated into the composition to indicate the presence of the cleansing composition in the solution.

The effervescent activity of these solution-forming cleansing compositions has conventionally been provided by the inclusion in the composition of the ingredients sodium bicarbonate and citric acid. Correspondingly, the reaction of these two ingredients has taken place at a pH that is weakly acidic or neutral, with a sacrifice in the efficiency and speed of cleaning, that would be achieved by the employment of a composition operable at a more basic pH.

The employment of the colorant in the composition as an indicator has been for the purpose of not only indicating the presence and activity of the cleansing composition, but serves to indicate by its disappearance the cessation of cleaning activity. For example, in the instance where denture cleansers are prepared, a dye component is included as an indicator to signify by coloration the presence of the cleansing composition and the commencement of its activity. In these applications, the actual period of activity is reasonably finite, and is predetermined by the manufacturer.

Accordingly, as the indicator or dye signals the user that the cleaning process has ended, attempts have been made to control the disappearance or fading of the dye, so that the disappearance of the dye will coincide with the completion of the cleaning cycle. Attempts to control the time span of the dye component have included the addition of limited quantities of dye, and the inclusion of additional amounts of bleaching agents to cause the dye to fade more quickly. The first approach has been generally unsuccessful, and the second approach proved uneconomical; the inclusion of additional bleach to fade the dye frequently required additional dye to be added to the composition to give the appropriate depth of initial coloration, and in turn required additional bleach to be added for fade control.

The present invention is believed to provide solutions to the aforementioned problem.

SUMMARY OF THE INVENTION

A cleansing composition is prepared in accordance with the present invention which comprises at least one oxidizing agent including an alkali metal monopersulfate salt, said oxidizing agent present in amounts ranging from 35-60%, a bleaching promoter selected from the group consisting of alkaline metal and alkaline earth metal halides, said bleaching promoter present in an amount of up to about 20%, and a compound selected from the group consisting of alkali metal and alkaline earth metal perborates, present in an amount sufficient to catalytically promote the effervescence of the cleansing composition. The composition after dissolution, provides a solution which possesses a pH in the basic range and includes sodium carbonate in an amount that may range from 20-40%. Sodium hydroxide may also be added in amounts of up to 0.5% to assist in pH maintenance.

Preferably, the oxidizing agent may comprise potassium monopersulfate, and may be present in an amount ranging from 40-50%. Sodium chloride may comprise the bleaching promoter, and may be present in an amount ranging from 10-20%, and the perborate compound may comprise sodium perborate and may be present in an amount ranging from 0.5-20%.

Solutions containing the present cleansing composition possess effervescing capability within an alkaline pH, due to the presence of the perborate compound. The perborate is theorized to react with the oxidizing agent and the bleaching promoter to initiate effervescence. The ability of these solutions to achieve effervescence within a basic pH range yields improved cleaning efficiency at reduced cost.

The present cleansing composition may also contain various additives, such as colorants, including dyes, perfumes, and the like. The cleansing composition may be prepared in tablet form, and may accordingly also include tableting agents, excipients, disintegrants and the like. In this latter form, the cleansing composition is particularly useful as a denture cleanser.

In accordance with the further embodiment of the present invention, a cleansing composition may be prepared which comprises an oxidizing agent containing a monopersulfate salt in an amount of from 35%–60%, a bleaching promoter selected from the group consisting of alkali metal and alkaline earth metal halides, present in an amount ranging up to about 20%, an effervescence promoting compound selected from alkaline earth metal and alkali metal perborates, present in amounts from about 0.5 to 20%, a colorant selected from pigments and dyes, and preferably comprising non-toxic dyes, the colorant present in an amount that may range as high as 1%, and a fade control agent comprising a compound capable of providing soluble halide ion. The halide component of said fade control agent may be selected from bromide, iodide and chloride ion, and is preferably selected from bromide and iodide.

The fade control agent is theorized to coact with the oxidizing agent in a catalytic manner that may abruptly accelerate the fading of the colorant. The fade control agent is particularly useful in the instance where the colorant comprises those dyes certified by the Food and Drug Administration as acceptable for use in foods, drugs and cosmetics, and known as F.D. & C. grade dyes. Also, D. & C. grade dyes, and insoluble dyes, such as F. D. & C. and D. & C. grade lakes may be utiized. C. grade may also be used.

The amount of fade control agent present in the cleansing composition of the present invention varies with the amount of dye and oxidizing agent present in the composition, and to a lesser extent, the amount of perborate salt included therein. In a preferred embodiment, the fade control agent may comprise potassium bromide, and may be present in amounts ranging from 0.04 to 0.3%.

The fade control agent acts in an unexpected catalytic manner and is particularly useful in the instance where the composition is prepared in tablet form as a denture cleanser. The dissolving tablet has been found to provide an initially strong, intensely colored solution. This intense color may be maintained for varying periods of time, depending on the desired quantities of colorant, perborate, oxidizing agent and fade control agent utilized.

By use of a particular quantity of the fade control agent, the color intensity of the solution can be maintained for a predetermined period of time; after which the fading of the color becomes noticeably accelerated, and a substantially colorless solution is thereafter rapidly obtained. For example, increments of as little as 0.1 milligram of the fade control agent have been found to vary the fade time of the dyes utilized in denture cleanser tablets prepared in accordance herewith, by as much as 1 minute; thus, the addition of 0.1 milligram of the fade control agent has been found to reduce the time it takes for the dyes to completely disappear by as much as 1 minute.

The foregoing compositions are useful in a variety of applications, apart from their preparation into denture cleanser tablets. Thus, for example, the compositions of the present invention may additionally be prepared as household cleansers, such as laundry bleaches and toilet bowl cleansers, and the like. Depending upon the desired applications, the cleansing compositions including those having the fade control agent, may include additional ingredients, such as soaps, perfumes, flavorings, and the like that may range in total amount as high as 5–10%. Preferably, these additional ingredients are present in amounts of up to about 5%.

As used throughout the present specification, all percentages are intended to be percent by weight.

Accordingly, it is a principal object of the present invention to prepare cleansing compositions capable of effervescing within a basic pH range.

It is a further object of the present invention to provide cleansing compositions including certain colorants, which compositions are capable of modification to control the presence of the color reaction.

It a yet further object of the present invention to prepare cleansing compositions as aforesaid which may be particularly utilized as denture cleansers.

It a yet further object of the present invention to provide cleansing compositions as aforesaid which are inexpensively prepared and reliable in use.

Other objects and advantages will become apparent to those skilled in the art from a consideration of the ensuing description.

DETAILED DESCRIPTION

The effervescing cleansing compositions of the present invention comprise an oxidizing agent that may be an alkali metal monopersulfate salt, present in an amount ranging from 35–60%, and preferably 40–50% by weight. The alkali metal monopersulfate salts are preferably the potassium or sodium salts, which are commercially available. The potassium salt is preferred, and may, if desired, be employed in the form of a triple salt with potassium bisulfate and potassium sulfate, e.g., $KHSO_5 \cdot KHSO_4 \cdot K_2SO_4$.

In the mole ratio of about 2:1:1, the foregoing triple salt is known commercially by the trademark "OXONE ®" and is sold by E. I. duPont DeNemours & Co., Inc.

The bleaching promoter or component is likewise well known, and may be selected from the group consisting of alkali and alkaline earth metal halides, in amounts ranging up to 20%, and preferably ranging from 10–20% by weight of the composition. The halide salt is preferably selected from alkaline metal halides such as the sodium and potassium salts. In a preferred embodiment, sodium chloride is utilized in an amount ranging between 10 and 20%.

The effervescence promoting compounds comprise the perborate salts, including the alkali metal and alkaline earth metal perborates. Preferably, the perborate salts are selected from the alkali metal salts, such as sodium and potassium, and a preferred embodiment, sodium perborate monohydrate is utilized. The perborate compounds unexpectedly promote effervescence by their reaction with the halide component. The perborate compounds are theorized to react as reducing agents, thereby recycling the halide to react in turn with the oxidizing agent to promote greater effervescence.

The perborate compounds may be present in amounts ranging from about 0.5 to 20%, and preferably from 0.7 to 15%.

As noted earlier, solutions obtained from the cleansing compositions possess a pH in the basic or alkaline range, which results in improved stain and soil removing capabilities. In a preferred embodiment, the pH of solutions obtained from the present compositions may range as high as pH 11, and preferably resides within the pH of 8 to 10. In the instance where the present compositions are formulated as denture cleansers, the preparation of compositions whose solutions will possess a pH within the aforementioned range facilitates the rapid removal of stains, with a reduction in the time that the dentures must reside in the cleansing solution, to as low as five minutes in some instances.

In addition to promoting effervescence in an alkaline or basic pH, the perborate compounds react favorably with the chloride bleaching promotors to reduce or eliminate the irritating odor and aftertaste caused by the presence of the hyphochlorite resulting from the reaction of the chloride salt with the oxidizing agent. The elimination of the hypochlorite odor permits the present compositions to be modified by the addition of perfuming agents and flavors, in the instance where the present compositions are to be formulated for use as denture cleansers.

As noted earlier, the cleansing compositions described above may be prepared in various formulations, and, accordingly, may contain certain additional ingredients selected on the basis of desired end use. Thus, for example, the compositions may include additional detergent compounds, including organic and inorganic detergents, including non-ionic detergents such as the various polyoxyethylene ethers of aromatic and aliphatic alcohols, as well as the polyoxyethylene ethers of hydrophobic propylene oxide polymers. These compounds assist in maintaining a foaming action, in the instance where the cleansing compositions are placed in aqueous solution.

Also, the compositions may contain other adjuvant materials, that may be inorganic or organic in structure. Thus, inorganic water-soluble alkaline builders such as alkali and alkaline earth metal carbonates, tetrapyophosphates, tripolyphosphates, phosphates, metasilicates and hydroxides, and mixtures of these may be added. Particularly, sodium carbonate may be present in an amount ranging from 20 to 40%, and preferably in an amount of from 25 to 30%, as it functions not only as a builder, but enhances effervescence and assists in stablizing the pH of the solutions obtained from the composition. In this latter capacity, sodium hydroxide may be added to assist in pH stabilization and may be present in amounts of up to about 0.5%, and preferably 0.3% to 0.5%.

The present compositions may also contain sequestrants for the purpose of maintaining solution clarity, in the instance where the compositions are placed in solution. Sequestrants useful in the present invention include ethylene diamine tetraacetic acid (EDTA) and its corresponding alkali salts, as well as other polyfunctional organic acids, such as citric acid, maleic acid, and their corresponding salts. The sequestrants may be present in amounts of up to about 3.5%, and preferably 0.3% to 3.5% by weight of the composition.

In the instance where the composition is to be prepared for use as a denture cleanser, other additives such as flavorings, colorants, perfumes and the like may be added in various amounts, as mentioned earlier. For example, the flavorings may include varieties of mint. These materials may be included and blended in various combinations within the scope of the present invention. The choice of the required amounts is likewise within the skill of the art.

In the instance where the present cleansing compositions are formulated for use as denture cleansers, the colorants useful herein are those known as F. D. & C. and D. & C. dyes and lakes. These materials are certified by the Federal Food and Drug Administration as acceptable for use in food, drug and cosmetic applications, and drug and cosmetic colorings. The materials acceptable for the foregoing spectrum of use are preferably water-soluble, and include indigoid dye, known as F. D. & C. Blue No. 2, which is the disodium salt of 5,5'-indigotindisulfonic acid. Similarly, the dye known as F. D. & C. Green No. 1, comprises a triphenylmethane dye and is the monosodium salt of 4-[4-(N-ethyl-p-sulfobenzylamino)diphenylmethylene]-[1-(N-ethyl-N-p-sulfoniumbenzyl)-$\Delta$ $^{2,5}$-cyclohexadienimine]. A full recitation of all F. D. & C. and D. & C. and their corresponding chemical structures may be found in the Kirk-Othmer Encyclopedia of Chemical Technology, at Volume 5, pages 857–884, which text is accordingly incorporated herein by reference. Dyes and colorants will fade at different rates and may be chosen to provide specific end points.

The foregoing colorants may be blended with each other in a variety of combinations. It is particularly desirable that the colorants be chosen so that the composition when initially dissolved will present a deep hue. This is important in the instance where the composition serves as a denture cleanser, as the fading phenomenon embodied in denture cleansers can be more easily observed by the end user.

In accordance with a further embodiment of the invention, the effervescing cleansing compositions may be prepared to include a fade control agent, in the instance where the compositions contain a colorant such as previously described, and are to be utilized in applications where cessation of composition activity is signified by disappearance of the color. The fade control agent comprises a compound providing soluble halide ion. The halide component of the fade control agent may be selected from bromide, iodide and chloride ion, and is preferably selected from bromide and iodide ion.

The amount of fade control agent present in the composition may vary, depending upon the end utility of the composition, as the fade time of the colorants employed will vary with the colorants, and with the end use to which the composition is put. For example, in the instance where the composition is to be utilized as a denture cleanser, it is desirable that the fade control agent be present in an amount sufficient to cause the total disappearance of the colorant within 18 minutes after a composition containing the colorant is placed in solution. Naturally, the amount of fade control agent present may be adjusted to accelerate the fading reaction and correspondingly to reduce the fade time.

One of the surprising aspects of the present invention, is that the fade control agents set forth herein operate in a catalytic manner, in that minute quantities of the fade control agents can achieve substantial and precise fade time control. For example, in the instance where a denture cleanser tablet is prepared having a weight of approximately 3.3 grams, with a content of about 4 milligrams of colorant, the addition of 1 milligram of the fade control agent can effect the reduction of the fade time of the colorant to within about 12 minutes. Moreover, the inclusion of an additional 0.1 milligram of the fade control agent to the denture cleanser tablet causes a reduction of 1 minute in the fade time.

The foregoing results are particularly advantageous in that the addition of the present fade control agent does not adversely effect the initial color reaction of the composition when placed in an aqueous solution. Prior art attempts to control fade time by the addition of greater quantities of bleaches and the like, have adversely effected the initial color reaction of the tablet, and have therefore been undesirable for use.

The particular fade control agents useful in accordance with the present invention comprise those compounds selected from the group consisting of the alkali metal salts of bromine, chloride and iodine, individually or in mixtures with each other. The potassium salts of these compounds are generally preferred, and more particularly, the compounds potassium bromide and potassium iodide have been found to be most effective.

The fade control agents may be added to the cleansing compositions in amounts ranging from about 0.04 to about 0.3% by weight of the composition. Preferably, the fade control agents may be present in an amount ranging from 0.04 to 0.18% by weight.

The compositions of the present invention are capable of preparation by a variety of techniques, depending upon the intended end use. In the instance where the present compositions are to serve as denture cleansers, it is desirable to prepare the compositions in tablet form. The use of the present compositions in tablet form is commercially preferred, as it is easier to achieve the uniformity of quantity and distribution of the ingredients of the compositions that is necessary to assure the corresponding uniformity of performance of the denture cleanser. Thus, cleanser tablets have been found to exhibit uniformity of color reaction, disintegration and fade time, and cleaning ability on a tablet-to-tablet basis.

To enable the present composition to be prepared in tablet form, certain ingredients, including excipients, tableting agents and the like are added, and the resulting composition is then compressed to form the final tablet. The particular tableting additives utilized herein comprise conventional materials normally utilized for such purpose, and may be selected and employed in amounts determined within the skill of the art.

In the instance where the contemplated composition is to contain a halide such as sodium chloride, it is advisable to add the basic component such as sodium carbonate to the ingredients prior to adding the monopersulfate salt, in order to avoid undue or premature reactivity of the resulting mixture.

A fuller understanding of the present invention will be gained from a review of the following illustrative examples. Compositions representing both the alkaline effervescing system, and the fade control agent are included. Unless specified otherwise, all amounts expressed as percent are deemed to be percent by weight of the total composition.

EXAMPLES 1-9

A series of compositions were prepared for use as denture cleansers, and comprised the ingredients set forth in Table 1, below.

The compositions were prepared in tablet form, each tablet weighing approximately 3.3 grams. The tablets were thereafter immersed in approximately 125 milliliters of water maintained at a temperature of about 45° C. The color reaction, disintegration time, pH and fade time were noted.

| INGREDIENTS | QUANTITIES, WEIGHT % EXAMPLE NO. | | | | | | | | |
|---|---|---|---|---|---|---|---|---|---|
| | 1 | 2 | 3 | 4 | 5 | 6 | 7 | 8 | 9 |
| 1. Sodium Chloride | 14.7 | 15 | 15 | 15 | 15 | 15 | 16 | 12.1 | 12.1 |
| 2. Sodium Hydroxide 50% Solution | .3 | .3 | .3 | .45 | .45 | .45 | — | — | — |
| 3. Potassium Bromide | .04 | .04 | .04 | .03 | .04 | .05 | — | — | — |
| 4. Water, Potable USP | .17 | .75 | .75 | .06 | .06 | .06 | — | — | — |
| 5. Sodium Carbonate Anhydrous | 29 | 28 | 28 | 29 | 29 | 29 | 25 | 25.8 | 26.3 |
| 6. Trisodium Phosphate, Anydrous, Food Grade, Granular | .45 | .9 | .9 | .45 | .45 | .45 | — | 2.5 | .9 |
| 7. Potassium Monopersulfate Compound | 48.3 | 50 | 48 | 49 | 49 | 49 | 49.4 | 48.7 | 49.6 |
| 8. Ethylenediaminetetraacetic Acid Tetrasodium Salt Dihydrate/Pure | .75 | .75 | 3.0 | .75 | .75 | .75 | .7 | .7 | .7 |
| 9. Sodium Perborate Monohydrate | 4.2 | 4.0 | 4.0 | 4.0 | 4.2 | 4.2 | 4.9 | 7.3 | 7.4 |
| 10. FD&C Blue Colors, mixed | .23 | .41 | .4 | .23 | .23 | .23 | .08 | .2 | .2 |
| 11. Flavor and Fragrance | .94 | .92 | .91 | .94 | .94 | .94 | .9 | .99 | .99 |
| 12. Detergent | .18 | .18 | .18 | .18 | .18 | .18 | 0.3 | .1 | .1 |
| 13. Tablet Lubricants | .72 | .28 | .28 | .72 | .72 | .72 | — | 0.5 | 0.5 |

Each of the tablets disintegrated within 5 minutes, and exhibited initially a strong color reaction, generally bluish on the basis of the dyes included in the colorants. Favorable effervescence was likewise observed, and the pH of the solutions of each of the compositions ranged between 9.0 and 9.6. In the instance where the compositions contained the fade control agent, fade time for the colorant ranged between 7 and 17 minutes.

EXAMPLE 10

The composition similar to that of Example 1, incremental additions of potassium iodide were made, after tablets of the composition were placed in separate containers holding 125 milliliters of water, maintained at a temperature of 45 degrees C. Four such containers were prepared having the incremental additions of potassium iodide set forth in Table 2 below.

TABLE 2

| SAMPLE NO. | POTASSIUM IODIDE ADDED (mg) | FADE TIME (min). |
|---|---|---|
| 1 | 0 (Control) | 12 |
| 2 | 0.5 | 10 |
| 3 | 1.0 | 9 |
| 4 | 1.5 | 8 |
| 5 | 2.0 | 7 |

It is apparent from a review of Table 2, above that 0.5 milligram incremental additions of potassium iodide effected substantial incremental reductions in the fade time, the most significant change being that of 2 minutes reduction upon the addition of the first 0.5 milligram increment. It is apparent from the above that substantial fade time reductions can be achieved with minimal incremental additions of the fade control agents.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. An effervescent cleansing composition comprising:
   (a) an oxidizing agent comprising a monopersulfate salt in an amount of from 35 to 60% by weight;
   (b) a bleaching promoter comprising an alkali metal or alkaline earth metal chloride in an amount of 10% to 20% by weight;
   (c) an effervescence promoting compound comprising a perborate salt, in an amount of from 0.5% to 20% by weight;
   (d) sodium carbonate in an amount of from 20% to 40% by weight;
   (e) sodium hydroxide in an amount of up to about 0.5% by weight;
   (f) a colorant, comprising at least one food, drug and cosmetic grade, or drug and cosmetic grade dye or lake, in an amount of from about 0.15% to 0.5% by weight; and,
   (g) a fade control agent comprising a compound selected from the group consisting of alkali metal bromides, alkali metal iodides and mixtures thereof, in an amount of from 0.04% to 0.3% by weight to control the time in which the colorant disappears.

2. The composition of claim 1 wherein said fade control agent is present in an amount of from 0.04 to 0.18% by weight.

3. The composition of claim 1 wherein said fade control agent is selected from the group consisting of potassium bromide, potassium iodide and mixtures thereof.

4. The composition of claim 1 further including at least one material selected from the group consisting of builders, detergents, lubricants, sequestrants, perfumes, flavorings, excipients, tableting agents, disintegrants and mixtures thereof.

5. The composition of claim 4 wherein said builders include sodium carbonate and trisodium phosphate, and said sequestrants comprise ethylene diamine tetraacetic acid and its alkali metal salts.

6. The composition of claim 5 whrein said builders are present in an amount of up to 40% by weight, and said sequestrant is present in an amount of from 0.3 to 3.5% by weight.

7. A tablet useful as a denture cleanser comprising the composition of claim 4.

8. The tablet useful as a denture cleanser comprising the composition of claims 2, 5 or 6.

9. An effervescent cleansing composition consisting essentially of:
   (a) an oxidizing agent comprising a monopersulfate salt in an amount of from 35% to 60% by weight;
   (b) a bleaching promoter selected from the group consisting of alkali metal and alkaline earth metal chlorides, said bleaching promoter present in an amount of up to about 20% by weight;
   (c) an effervescence promoting compound comprising a perborate salt, present in an amount of from 0.5 to 20% by weight;
   (d) a colorant comprising at least one food, drug and cosmetic grade dye or lake, in an amount of from about 0.15 to 0.5% by weight;
   (e) a fade control agent selected from the group consisting of the alkali metal bromides, alkali metal iodides, and mixtures thereof, in an amount of from 0.04 to 0.3% by weight; and
   (f) said effervescence cleansing composition effervescing at an alkaline pH when placed in solution.

10. The composition of claim 9 wherein said fade control agent is selected from the group consisting of potassium bromide, potassium iodine and mixtures thereof.

11. The composition of claim 9 wherein said fade control agent is present in an amount of from about 0.04 to 0.18% by weight.

12. The composition of claim 10 wherein said fade control agent is present in an amount of from about 0.04 to 0.18% by weight.

13. The composition of claim 9 further including at least one material selected from the following: builders, sequestrants, detergents, perfumes, flavorings, exipients, pH stabilizers, tableting agents, disintegrants, and mixtures thereof.

14. The composition of claim 13 wherein said builders are selected from the group consisting of alkali metal carbonates, alkali metal phosphates, and mixtures thereof; said sequestrants comprise polyfunctional organic acids and their alkali metal salts; and said pH stabilizers comprise sodium hydroxide.

15. The composition of claim 14 wherein said builders are selected from the group consisting of sodium carbonate, trisodium phosphate and mixtures thereof, and are present in a total amount ranging from 20 to 40% by weight; said sequestrants comprise the alkali metal salts of ethylenediamine tetraacetic acid in an amount of from 0.3 to 3.5% by weight; and said colorants are selected from food, drug and cosmetic grade dyes or lakes having the individual colors blue, red and green, and mixtures thereof.

16. A tablet useful as a denture cleanser comprising the composition of either of claims 9, 10, 11 or 12.

* * * * *